United States Patent
Van Tol et al.

(10) Patent No.: US 9,987,075 B2
(45) Date of Patent: *Jun. 5, 2018

(54) SURGICAL INSTRUMENT WITH END-EFFECTOR ASSEMBLY INCLUDING THREE JAW MEMBERS

(71) Applicant: COVIDIEN LP, Mansfield, MA (US)

(72) Inventors: David J. Van Tol, Boulder, CO (US); Anthony B. Ross, Boulder, CO (US); Alexander M. Waskiewicz, Lafayette, CO (US); Eric R. Larson, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 539 days.

This patent is subject to a terminal disclaimer.

(21) Appl. No.: 14/548,919

(22) Filed: Nov. 20, 2014

(65) Prior Publication Data

US 2015/0150573 A1 Jun. 4, 2015

Related U.S. Application Data

(60) Provisional application No. 61/910,669, filed on Dec. 2, 2013.

(51) Int. Cl.
| | |
|---|---|
| A61B 18/14 | (2006.01) |
| A61B 18/12 | (2006.01) |
| A61B 18/00 | (2006.01) |
| A61B 17/29 | (2006.01) |
| A61B 17/32 | (2006.01) |

(52) U.S. Cl.
CPC ......... *A61B 18/1445* (2013.01); *A61B 17/29* (2013.01); *A61B 18/1447* (2013.01); *A61B 18/1482* (2013.01); *A61B 17/320092* (2013.01); *A61B 18/1206* (2013.01); *A61B 2017/2926* (2013.01); *A61B 2017/2929* (2013.01); *A61B 2017/2938* (2013.01); *A61B 2018/0063* (2013.01); *A61B 2018/00601* (2013.01)

(58) Field of Classification Search
CPC ............ A61B 18/1442; A61B 18/1445; A61B 2018/1455; A61B 2018/1452; A61B 2017/2947; A61B 2017/2948; A61B 2017/2906

See application file for complete search history.

(56) References Cited

U.S. PATENT DOCUMENTS

| | | | |
|---|---|---|---|
| 4,174,715 A | 11/1979 | Hasson | |
| 5,776,075 A | 7/1998 | Palmer | |
| 5,976,161 A | 11/1999 | Kirsch et al. | |
| 6,083,223 A * | 7/2000 | Baker | A61B 18/1445 606/49 |
| 6,139,508 A | 10/2000 | Simpson et al. | |
| 9,237,900 B2 * | 1/2016 | Boudreaux | A61B 17/282 |

(Continued)

*Primary Examiner* — Ronald Hupczey, Jr.
*Assistant Examiner* — Bo Ouyang

(57) ABSTRACT

A surgical device includes an elongated shaft having an end-effector assembly at a distal end thereof. The end-effector assembly includes movable first, second and third jaw members. The first and second jaw members controllably movable from a first position, wherein the first and second jaw members are disposed in spaced relation relative to the third jaw member disposed therebetween, to a second position, wherein the first, second and third jaw members cooperate to grasp tissue therebetween.

14 Claims, 10 Drawing Sheets

(56) References Cited

U.S. PATENT DOCUMENTS

| | | | |
|---|---|---|---|
| 2003/0018331 A1* | 1/2003 | Dycus | A61B 18/1485 |
| | | | 606/48 |
| 2005/0124912 A1 | 6/2005 | Griego et al. | |
| 2005/0182426 A1 | 8/2005 | Adams et al. | |
| 2005/0267529 A1 | 12/2005 | Crockett et al. | |
| 2007/0244510 A1 | 10/2007 | Weizman et al. | |
| 2010/0016883 A1 | 1/2010 | Christoudias | |
| 2010/0137854 A1* | 6/2010 | Hosier | A61B 18/12 |
| | | | 606/33 |
| 2010/0185196 A1* | 7/2010 | Sakao | A61B 18/1445 |
| | | | 606/51 |
| 2011/0077668 A1 | 3/2011 | Gordon et al. | |
| 2012/0083783 A1* | 4/2012 | Davison | A61B 18/1445 |
| | | | 606/45 |
| 2012/0239080 A1 | 9/2012 | Fan | |
| 2013/0085494 A1 | 4/2013 | Weisenburgh, II et al. | |

\* cited by examiner

SURGICAL INSTRUMENT WITH END-EFFECTOR ASSEMBLY INCLUDING THREE JAW MEMBERS

CROSS REFERENCE TO RELATED APPLICATION

The present application claims the benefit of and priority to U.S. Provisional Application Ser. No. 61/910,669, filed on Dec. 2, 2013, the entire contents of which are incorporated herein by reference.

BACKGROUND

1. Technical Field

The present disclosure relates to surgical instruments such as electrosurgical and ultrasonic devices. More particularly, the present disclosure relates to end-effector assemblies including three jaw members for use in surgical instruments to grasp, seal and/or cut tissue.

2. Discussion of Related Art

Electrosurgical and ultrasonic devices have become widely used by surgeons. Electrosurgery involves the application of thermal and/or electrical energy to cut, dissect, ablate, coagulate, cauterize, seal or otherwise treat biological tissue during a surgical procedure. Electrosurgery is typically performed using an electrosurgical generator operable to output energy and a handpiece including a surgical instrument (e.g., end effector) adapted to transmit energy to a tissue site during electrosurgical procedures. Electrosurgery can be performed using either a monopolar or a bipolar instrument.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode or pad that is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode. In bipolar electrosurgery, both the active electrode and return electrode functions are performed at the site of surgery. Bipolar electrosurgical devices include two electrodes that are located in proximity to one another for the application of current between their surfaces. Bipolar electrosurgical current travels from one electrode, through the intervening tissue to the other electrode to complete the electrical circuit. Bipolar instruments generally include end-effectors, such as grippers, cutters, forceps, dissectors and the like.

Forceps utilize mechanical action to constrict, grasp, dissect and/or clamp tissue. By utilizing an electrosurgical forceps, a surgeon can utilize both mechanical clamping action and electrosurgical energy to effect hemostasis by heating the tissue and blood vessels to cauterize, coagulate/desiccate, seal and/or divide tissue. Bipolar electrosurgical forceps utilize two generally opposing electrodes that are operably associated with the inner opposing surfaces of end effectors and that are both electrically coupled to an electrosurgical generator. In bipolar forceps, the end-effector assembly generally includes opposing jaw assemblies pivotably mounted with respect to one another. In a bipolar configuration, only the tissue grasped between the jaw assemblies is included in the electrical circuit. Because the return function is performed by one jaw assembly of the forceps, no patient return electrode is needed.

By utilizing an electrosurgical forceps, a surgeon can cauterize, coagulate/desiccate and/or seal tissue and/or simply reduce or slow bleeding by controlling the intensity, frequency and duration of the electrosurgical energy applied through the jaw assemblies to the tissue. During the sealing process, mechanical factors such as the pressure applied between opposing jaw assemblies and the gap distance between the electrically-conductive tissue-contacting surfaces (electrodes) of the jaw assemblies play a role in determining the resulting thickness of the sealed tissue and effectiveness of the seal.

A variety of types of end-effector assemblies have been employed for various types of surgery, e.g., electrosurgery using a variety of types of monopolar and bipolar electrosurgical instruments.

SUMMARY

A continuing need exists for a reliable surgical instrument that assists in gripping, manipulating and holding tissue prior to and during activation and dividing of the tissue. A need exists for surgical instruments with an end-effector assembly suitable for use with a variety of energy sources.

According to an aspect of the present disclosure, a surgical device is provided. The surgical device includes an elongated shaft having an end-effector assembly at a distal end thereof. The end-effector assembly includes movable first, second and third jaw members. The first and second jaw members are controllably movable from a first position, wherein the first and second jaw members are disposed in spaced relation relative to the third jaw member disposed therebetween, to a second position closer to the third jaw member, wherein the first, second and third jaw members cooperate to grasp tissue therebetween.

According to another aspect of the present disclosure, an end-effector assembly operatively coupled to a shaft is provided. The end-effector assembly includes movable first, second and third jaw members. The first and second jaw members are pivotably mounted with respect to one another. The third jaw member is disposed between the first and second jaw members. The first and second jaw members are configured to be controllably movable from a first position, wherein the first and second jaw members are disposed in spaced relation relative to the third jaw member, to a second position closer to the third jaw member, wherein the first, second and third jaw members cooperate to grasp tissue therebetween.

BRIEF DESCRIPTION OF THE DRAWINGS

Objects and features of the presently-disclosed surgical instruments and end-effector assemblies including three jaw members for use in surgical instruments to grasp, seal and/or cut tissue will become apparent to those of ordinary skill in the art when descriptions of various embodiments thereof are read with reference to the accompanying drawings, of which.

DETAILED DESCRIPTION

Figure 1:
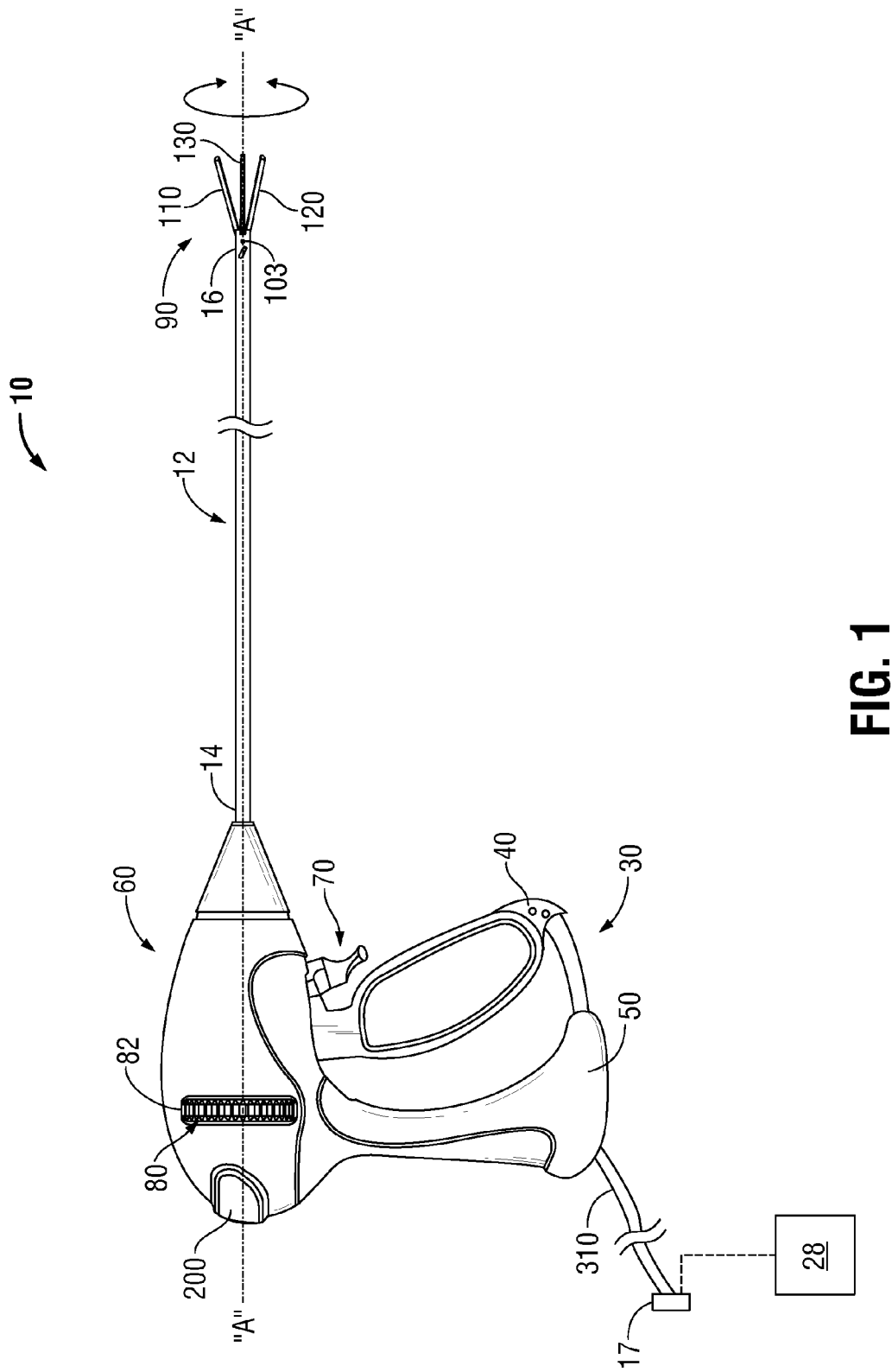
FIG. 1 is a right, side view of a surgical instrument showing a housing, a rotatable member, a shaft, and an end-effector assembly including three jaw members in accordance with an embodiment of the present disclosure.

Hereinafter, embodiments of surgical instruments of the present disclosure and end-effector assemblies including three jaw members for use in surgical instruments to grasp, seal and/or cut tissue of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

Various embodiments of the present disclosure provide surgical instruments suitable for sealing, cauterizing, coagulating/desiccating and/or cutting vessels and vascular tissue. Embodiments of the presently-disclosed surgical instruments with an end-effector assembly including three jaw members may be suitable for utilization in endoscopic surgical procedures and/or suitable for utilization in open surgical applications. Embodiments of the presently-disclosed surgical instruments may be implemented using a variety of types of energy, e.g., electrosurgical energy at radio frequencies (RF) or at other frequencies, ultrasonic, optical, and/or thermal energy.

The various embodiments disclosed herein may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

In FIG. 1, an embodiment of a surgical instrument 10 is shown for use with various surgical procedures, e.g., endoscopic surgical procedures. Surgical instrument 10 generally includes a housing 60, a handle assembly 30, a rotatable assembly 80, a trigger assembly 70, and an end-effector assembly 90 that mutually cooperate to grasp, seal and/or divide tissue (e.g., tissue "T" shown in FIGS. 3 and 4), e.g., tubular vessels and vascular tissue. End-effector assembly 90 includes a first jaw member 110, a second jaw member 120, and a third jaw member 130 disposed between the first and second jaw members 110 and 120, respectively, which are configured to be controllably movable, e.g., to grasp and/or seal tissue.

Figure 13:
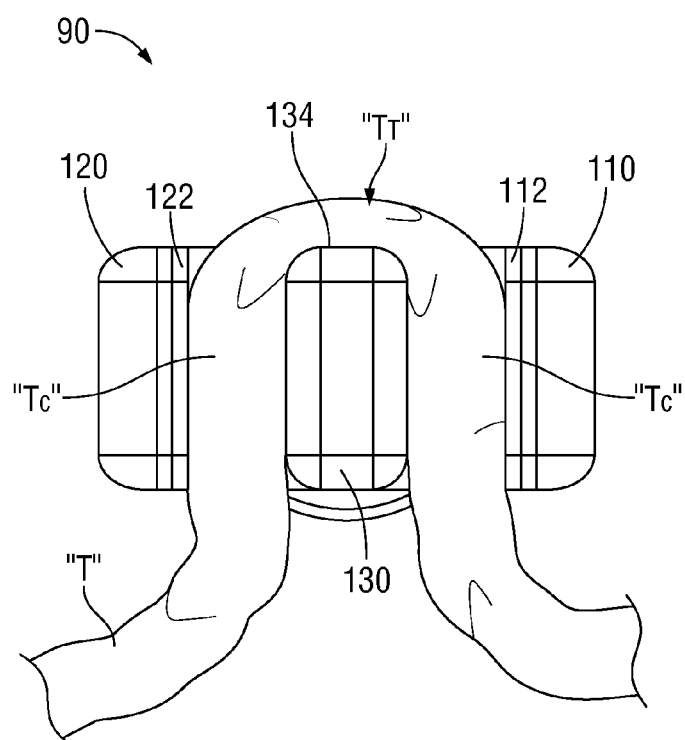
FIG. 13 is an enlarged, end view of the surgical instrument shown in FIG. 12, showing the first and second jaw members in a closed configuration with tissue in compression disposed between the electrically-conductive tissue-engaging surfaces of the third jaw member and the electrically-conductive tissue-engaging surfaces of the first and second jaw members, respectively, shown with tissue in tension overlying the upper surface of the third jaw member, in accordance with an embodiment of the present disclosure.

The first and second jaw members 110 and 120 are configured to be controllably movable relative to one another and/or relative to the third jaw member 130, e.g., to control the amount of compression applied to tissue (e.g., tissue in compression "$T_c$" shown in FIG. 13). In some embodiments, the instrument 10 is configured to provide a user capability to controllably move the first and second jaw members 110 and 120 laterally towards the third jaw member 130 to progressively tension tissue (e.g., tissue in tension "$T_T$" shown in FIG. 13) overlying the upper surface 134 of the third jaw member 130.

Surgical instrument 10 generally includes an elongated shaft 12 defining a longitudinal axis "A-A". Shaft 12 supports movement of other components therethrough, e.g., to impart movement to the first, second and third jaw members 110, 120 and 130, respectively. In some embodiments, the trigger assembly 70 is operatively coupled to the end-effector assembly 90, e.g., to allow the surgeon to change the position and/or orientation of the third jaw member 130.

Although FIG. 1 depicts a surgical instrument 10 for use in connection with endoscopic surgical procedures, the teachings of the present disclosure may also apply to more traditional open surgical procedures. For the purposes herein, the device 10 is described in terms of an endoscopic instrument; however, an open version of the device (e.g., surgical instrument 500 shown in FIG. 5) may also include the same or similar operating components and features as described below.

In some embodiments, as shown in FIG. 1, first jaw member 110 and the second jaw member 120 are pivotably connected about a pivot pin 103 and controllably movable relative to one another and/or the third jaw member 130. The first and second jaw members 110 and 120, respectively, may be curved at various angles to facilitate manipulation of tissue and/or to provide enhanced line-of-sight for accessing targeted tissues. The first, second, and third jaw members 110, 120, and 130, respectively, may be formed from any suitable material or combination of materials by any suitable process, e.g., machining, stamping, electrical discharge machining (EDM), forging, casting, injection molding, metal injection molding (MIM), and/or fineblanking. End-effector assembly 90 may include one or more electrically-insulative elements to electrically isolate the first jaw member 110 from the second jaw member 120. End-effector assembly 90 may additionally, or alternatively, include one or more electrically-insulative bushings to electrically isolate the third jaw member 130 from the first jaw member 110 and/or the second jaw member 120.

End-effector assembly 90 may include one or more electrically-conductive tissue-engaging surfaces (also referred to herein as "sealing plates") coupled to, or otherwise disposed in association with, the first, second and/or third jaw member 110, 120 and/or 130, respectively. In some embodiments, as shown in FIGS. 2A, 2B, 3 and 4, end-effector assembly 90 includes first and second electrically-conductive tissue-engaging surfaces or sealing plates 112 and 122, respectively, wherein the first electrically-conductive tissue-engaging surface or sealing plate 112 is coupled to, or otherwise disposed in association with, the first jaw member 110, and the second electrically-conductive tissue-engaging surface or sealing plate 122 is coupled to, or otherwise disposed in association with, the second jaw member 120. End-effector assembly 90 may include electrically-insulative members configured to electrically isolate, at least in part, the first and second sealing plates 112 and 122 from the first and second jaw members 110 and 120, respectively. In alternative embodiments, the first and second sealing plates 112 and 122 may be integrally formed with the first and second jaw members 110 and 120, respectively. End-effector assembly 90 may additionally, or alternatively, include electrically-conductive tissue-engaging surfaces or sealing plates coupled to, or otherwise disposed in association with, the third jaw member 130.

In some embodiments, as shown in FIGS. 2A through 6, the end-effector assembly 91 additionally includes third and fourth sealing plates 131 and 132 coupled to, or otherwise disposed in association with, the third jaw member 130, wherein the first and third sealing plates 112 and 131, respectively, are disposed in opposing relation to one another, and the second and fourth sealing plates 122 and 132, respectively, are disposed in opposing relation to one another. In some embodiments, the end-effector assembly 91 may be configured to allow the first, second, third and fourth sealing plates 112, 122, 131 and 132 to be separately activated, and/or activated in pairs (e.g., first and third sealing plates 112 and 131 and/or second and fourth sealing plates 122 and 132).

Figure 2A:
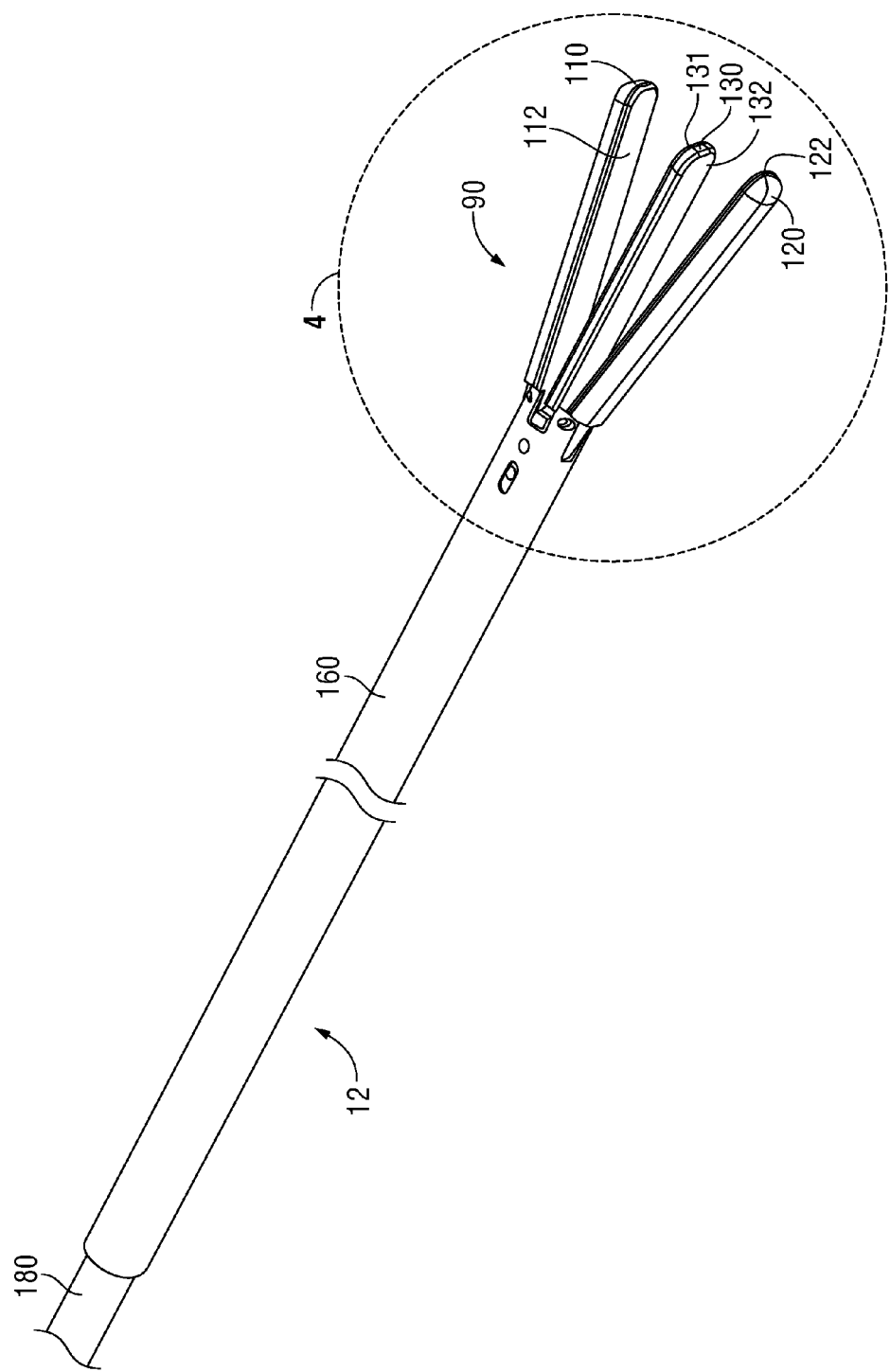
FIG. 2A is an enlarged, perspective view of a portion of the surgical instrument shown in FIG. 1, showing the end-effector assembly disposed in a first configuration wherein the first and second jaw members are spaced apart from the third jaw member disposed therebetween, in accordance with an embodiment of the present disclosure.
Figure 2B:
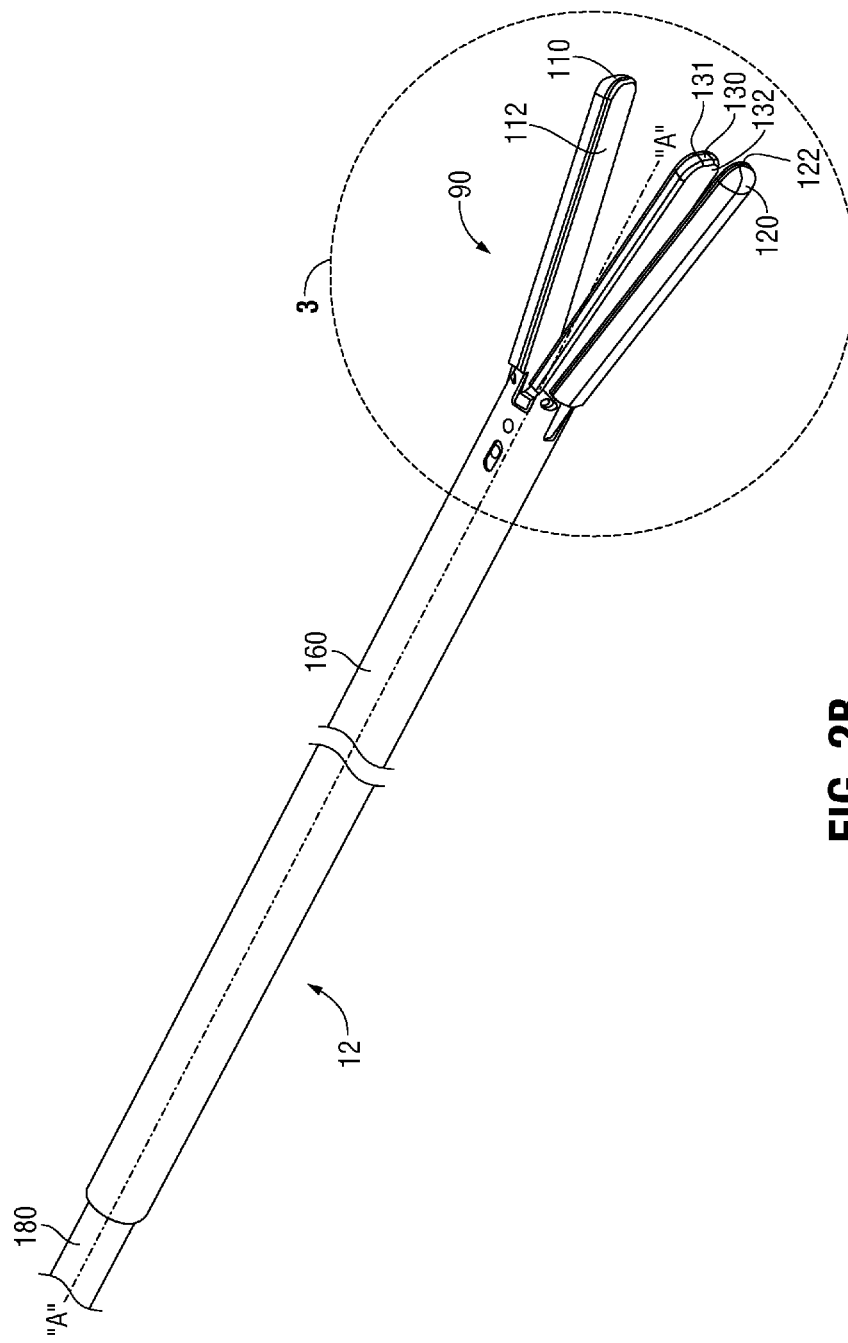
FIG. 2B is an enlarged, perspective view of the portion of the end-effector assembly of FIG. 2A, disposed in a second configuration wherein the first and second jaw members are disposed in spaced relation relative to the third jaw member shown slanted downward at a first angle, e.g., relative to a longitudinal axis defined by the shaft, in accordance with an embodiment of the present disclosure.

In some embodiments, as shown FIGS. 2A and 2B, shaft 12 includes an outer shaft member 160 and an inner shaft member 180 that is configured for longitudinal motion with respect to the outer shaft member 160. Inner shaft member 180 is slidingly disposed within the outer shaft member 160 and operable by a drive assembly (not shown). Embodiments of an elongated shaft that includes an outer shaft member (e.g., 760 shown in FIG. 7) and an inner shaft member (e.g., 780 shown in FIG. 7) are described in more detail later in this description.

As shown in FIG. 1, the shaft 12 includes a distal end 16 configured to mechanically engage the end-effector assembly 90. In some embodiments, the end-effector assembly 90 is selectively and releaseably engageable with the distal end 16 of the shaft 12. The proximal end 14 of the shaft 12 is received within the housing 60, and connections relating thereto are disclosed in commonly assigned U.S. Pat. No. 7,150,097 entitled "METHOD OF MANUFACTURING JAW ASSEMBLY FOR VESSEL SEALER AND DIVIDER," commonly assigned U.S. Pat. No. 7,156,846 entitled "VESSEL SEALER AND DIVIDER FOR USE WITH SMALL TROCARS AND CANNULAS," commonly assigned U.S. Pat. No. 7,597,693 entitled "VESSEL SEALER AND DIVIDER FOR USE WITH SMALL TROCARS AND CANNULAS," and commonly assigned U.S. Pat. No. 7,771,425 entitled "VESSEL SEALER AND DIVIDER HAVING A VARIABLE JAW CLAMPING MECHANISM."

Surgical instrument 10 includes a cable 310. Cable 310 may be formed from a suitable flexible, semi-rigid or rigid cable, and may connect directly to an energy source 28, e.g., an ultrasonic and/or electrosurgical power generating source. In some embodiments, the cable 310 connects the surgical instrument 10 to a connector 17, which further operably connects the instrument 10 to the energy source 28. Cable 310 may be internally divided into one or more cable leads (not shown) each of which transmits energy through its respective feed path to the end-effector assembly 90. In some embodiments, cable 310 may include optical fiber.

Energy source 28 may be any generator suitable for use with surgical devices, and may be configured to provide various frequencies of electrosurgical energy, optical energy, and/or ultrasound. Examples of electrosurgical generators that may be suitable for use as a source of electrosurgical energy are commercially available under the trademarks FORCE EZ™, FORCE FX™, and FORCE TRIAD™ offered by Covidien Surgical Solutions of Boulder, Colo. Surgical instrument 10 may alternatively be configured as a wireless device or battery-powered.

As shown in FIG. 1, the end-effector assembly 90 is rotatable about a longitudinal axis "A-A" through rotation, either manually or otherwise, of the rotatable assembly 80. Rotatable assembly 80 generally includes two halves (not shown), which, when assembled about the shaft 12, form a generally circular rotatable member 82. Rotatable assembly 80, or portions thereof, may be configured to house a drive assembly (not shown) or components thereof. Examples of rotatable assembly embodiments and drive assembly embodiments of the surgical instrument 10 are described in the above-mentioned, commonly-assigned U.S. Pat. Nos. 7,150,097, 7,156,846, 7,597,693 and 7,771,425.

Handle assembly 30 includes a fixed handle 50 and a movable handle 40. In some embodiments, the fixed handle 50 is integrally associated with the housing 60, and the movable handle 40 is selectively movable relative to the fixed handle 50. Movable handle 40 of the handle assembly 30 is ultimately connected to the drive assembly (not shown). As can be appreciated, applying force to move the movable handle 40 toward the fixed handle 50 pulls a drive element (e.g., inner shaft member 180) proximally to impart movement to the first and second jaw members 110 and 120 from an open position, wherein the first and second jaw members 110 and 120 are disposed in spaced relation relative to the third jaw member 130, to a clamping or closed position, wherein the first, second and third jaw members 110, 120 and 130 cooperate to grasp tissue therebetween. Examples of handle assembly embodiments of the surgical instrument 10 are described in the above-mentioned, commonly-assigned U.S. Pat. Nos. 7,150,097, 7,156,846, 7,597,693 and 7,771,425.

Surgical instrument 10 includes a switch 200 configured to permit the user to selectively activate the instrument 10 in a variety of different orientations, i.e., multi-oriented activation. As can be appreciated, this simplifies activation. When the switch 200 is depressed, energy is transferred through one or more pathways, e.g., electrical leads (not shown) and/or optical fiber (not shown), to the jaw members 110 and 120. Although FIG. 1 depicts the switch 200 disposed at the proximal end of the housing assembly 60, switch 200 may be disposed on another part of the instrument 10 (e.g., the fixed handle 50, rotatable member 82, etc.) or another location on the housing assembly 60.

FIG. 2A shows the end-effector assembly 90 disposed in a first configuration wherein the first and second jaw members 110 and 120 are spaced apart from the third jaw member 130 disposed therebetween. FIG. 2B shows the end-effector assembly 90 disposed in a second configuration wherein the third jaw member 130 is disposed slanted downward at a first angle, e.g., relative to the longitudinal axis "A-A" defined by the shaft 12 and/or relative to the first and second jaw members 110 and 120, respectively. In some embodiments, the first angle may be an acute angle, e.g., an angle that measures between 0 degrees and 90 degrees. When the end-effector assembly 90 is disposed in the second configuration, the distal end 131 of the third jaw member 130 is positioned offset from the longitudinal axis "A-A" defined by the shaft 12.

Figure 3:
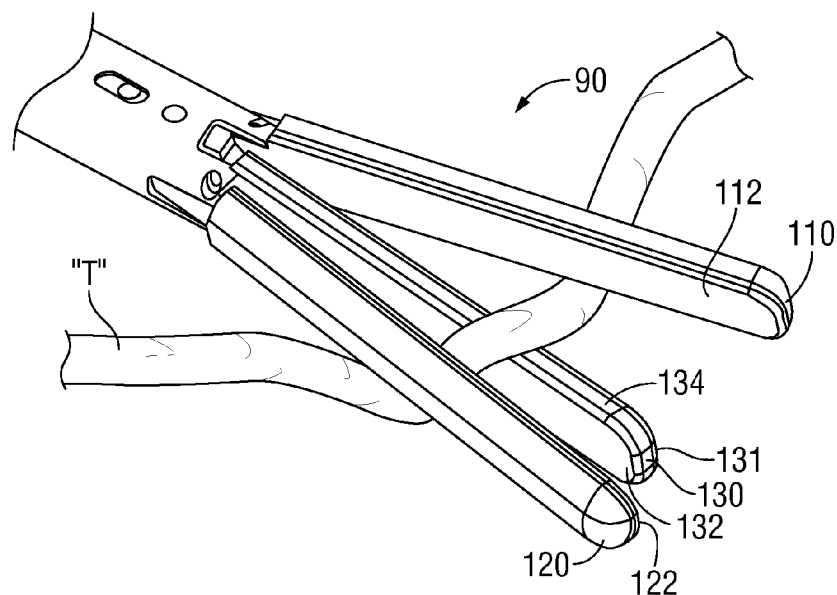
FIG. 3 is an enlarged, perspective view of the indicated area of detail of FIG. 2B showing the end-effector assembly disposed in the second configuration, shown with tissue disposed below the lower surfaces of the first and second jaw members and tissue overlying the upper surface of the third jaw member, in accordance with an embodiment of the present disclosure.
Figure 4:
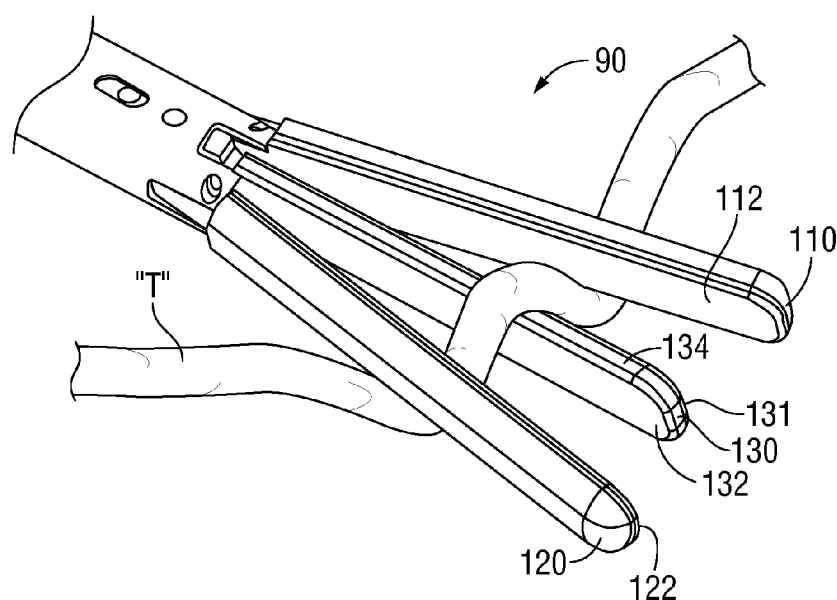
FIG. 4 is an enlarged, perspective view of the indicated area of detail of FIG. 2A showing the end-effector assembly disposed in the first configuration, shown with tissue disposed below the lower surfaces of the first and second jaw members and tissue overlying the upper surface of the third jaw member, in accordance with an embodiment of the present disclosure.

FIG. 3 shows tissue in contact with the first, second, and third jaw members 110, 120, and 130, respectively, of the end-effector assembly 90, which is disposed in the second configuration shown in FIG. 2B. FIG. 4 shows tissue in contact with the first, second, and third jaw members 110, 120, and 130, respectively, of the end-effector assembly 90, which is disposed in the first configuration shown in FIG. 2A.

Figure 5:
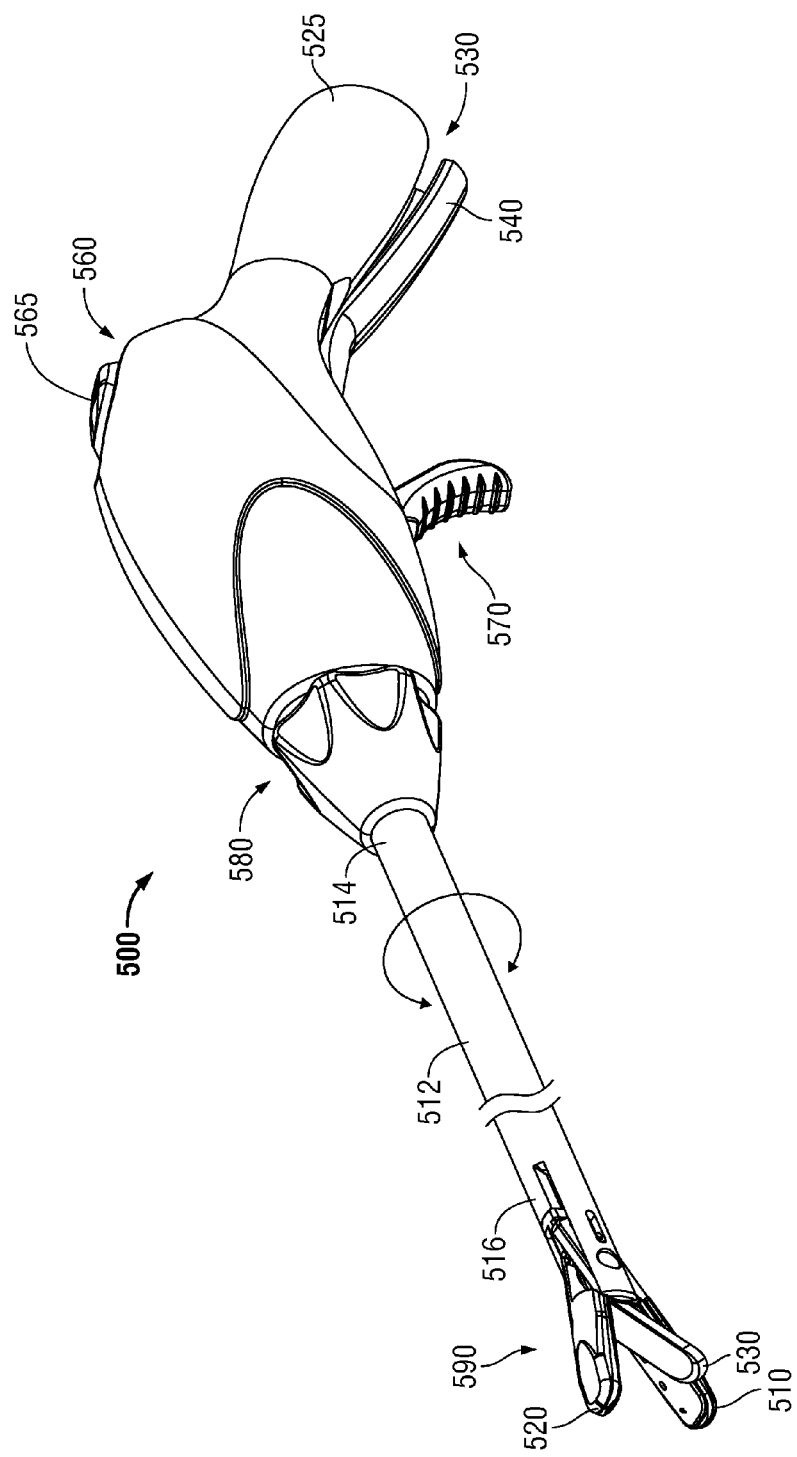
FIG. 5 is a left, side view of another embodiment of a surgical instrument showing a housing, a rotatable member, a shaft, and an end-effector assembly including three jaw members in accordance with the present disclosure.

In FIG. 5, an embodiment of a surgical instrument 500 is shown for use with various surgical procedures, e.g., open surgical procedures. Surgical instrument 500 generally includes a housing 560, a handle assembly 530, a rotatable assembly 580, a trigger assembly 570, and an end-effector assembly 590 that mutually cooperate to grasp, seal and/or divide tissue, e.g., tubular vessels and vascular tissue. An embodiment of the end-effector assembly 590 is shown in more detail in FIG. 6.

Surgical instrument 500 includes an elongated shaft 512 including a distal end 16 configured to mechanically engage the end-effector assembly 590. A proximal end 14 of the shaft 12 is received within the housing 60. The housing 560, the rotatable assembly 580, and the trigger assembly 570 are similar to the housing 60, the rotatable assembly 80, and the trigger assembly 70 shown in FIG. 1, and further description of the like elements is omitted in the interests of brevity.

End-effector assembly 590 includes a first jaw member 510, a second jaw member 520, and a third jaw member 530 disposed between the first and second jaw members 510 and 520. In some embodiments, as shown in FIG. 6, first jaw member 510 and the second jaw member 520 are pivotably connected about a pivot pin 503 and controllably movable relative to the third jaw member 530 disposed therebetween.

As shown in FIG. 5, the handle assembly 530 includes a fixed handle 525 and a movable handle 540. Movable handle 540 of the handle assembly 530 is connected to a drive assembly (not shown). As can be appreciated, applying force to move the movable handle 540 toward the fixed handle 525 pulls a drive element (e.g., inner shaft member 180) proximally to impart movement to the first and second jaw members 510 and 520 from an open position, wherein the first and second jaw members 510 and 520 are disposed in spaced relation relative to the third jaw member 530, to a clamping or closed position, wherein the first, second and third jaw members 510, 520 and 530, respectively, cooperate to grasp tissue therebetween.

Surgical instrument 500 includes a switch 565 configured to permit the user to selectively activate the instrument 500. When the switch 565 is depressed, energy is transferred through one or more pathways, e.g., electrical leads (not shown) and/or optical fiber (not shown), to the jaw members 510 and 520.

Figure 6:
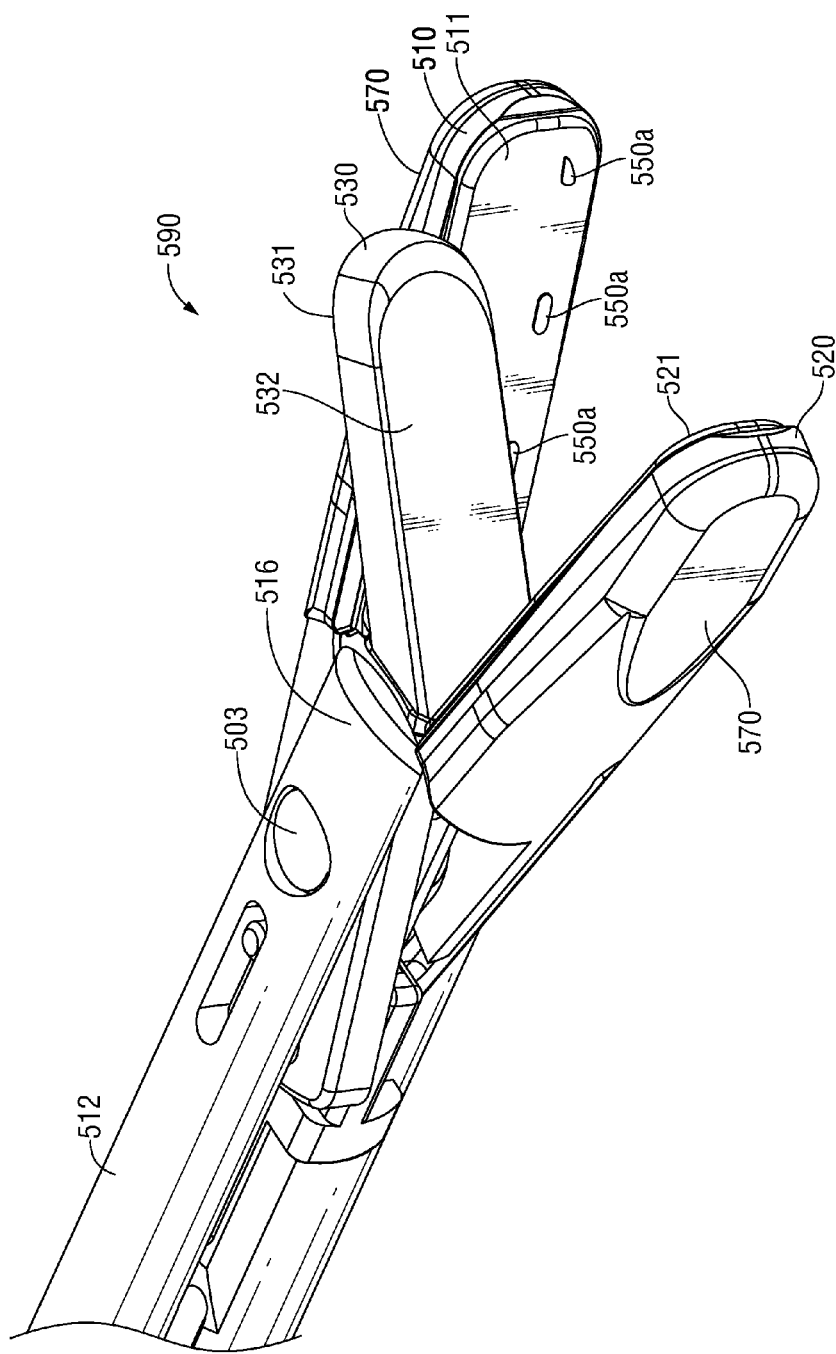
FIG. 6 is an enlarged, perspective view of the distal end of the surgical instrument shown in FIG. 5 showing the end-effector assembly including the first, second and third jaw members in accordance with the present disclosure.

As shown in FIG. 6, the end-effector assembly 590 includes first and second electrically-conductive tissue-engaging surfaces 511 and 521, respectively. In some embodiments, the first electrically-conductive tissue-engaging surface 511 (also referred to herein as "first sealing plate 511") is coupled to, or otherwise disposed in association with, the first jaw member 510, and the second electrically-conductive tissue-engaging surface 521 (also referred to herein as "second sealing plate 521") is coupled to, or otherwise disposed in association with, the second jaw member 520. In some embodiments, a brazing material or adhesive material may be disposed between the first sealing plate 511 and the first jaw member 510 and/or between the second sealing plate 521 and the second jaw member 520, e.g., to facilitate assembly and/or provide strength and rigidity. In other embodiments, the first and second sealing plates 511 and 521 may be integrally formed with the first and second jaw members 510 and 520, respectively. The shape and size of the first and second sealing plates 511 and 521 may be varied from the configuration depicted in FIG. 6.

End-effector assembly 590 may additionally, or alternatively, include electrically-conductive tissue-engaging surfaces 531 and 532 (also referred to herein as "third and fourth sealing plates 531 and 532") coupled to, or otherwise disposed in association with, the third jaw member 530.

In some embodiments, end-effector assembly 590 includes a series of stop members 550a disposed on the inner-facing surface of the first sealing plate 511 and/or the second sealing plate 521. Stop members 550a, compatible with any of the above embodiments, may be configured to facilitate and/or enhance the gripping and manipulation of tissue and to control the gap distance (not shown) between the three jaw members during the sealing of tissue. Stop members 550a of varied configurations may be employed on the first jaw member 510, the second jaw member 520, and/or the third jaw member 530 depending upon a particular purpose or to achieve a desired result. Examples of stop member embodiments as well as various manufacturing and assembling processes for attaching and/or affixing the stop members 550a to the sealing plate surfaces are described in commonly-assigned International Application Serial No. PCT/US01/11413 filed on Apr. 6, 2001, entitled "VESSEL SEALER AND DIVIDER WITH NON-CONDUCTIVE STOP MEMBERS."

In some embodiments, as shown in FIG. 6, end-effector assembly 590 includes insulators 570 disposed on the first and second jaw members 510 and 520. An inner surface of the insulators 570 and/or an outer surface of the first and second jaw members 510 and 520 may include detents, tongue and groove interfaces, locking tabs, adhesive ports, etc., utilized either alone or in combination for assembly purposes. In some embodiments, the insulators 570 may be overmolded onto the first and second jaw members 510 and 520. End-effector assembly 590 may include additional, fewer, or different components than shown in FIGS. 5 and 6, respectively, depending upon a particular purpose or to achieve a desired result. The shape and size of the first, second and third jaw members 510, 520 and 530, respectively, may be varied from the configuration depicted in FIGS. 5 and 6.

Figure 7:
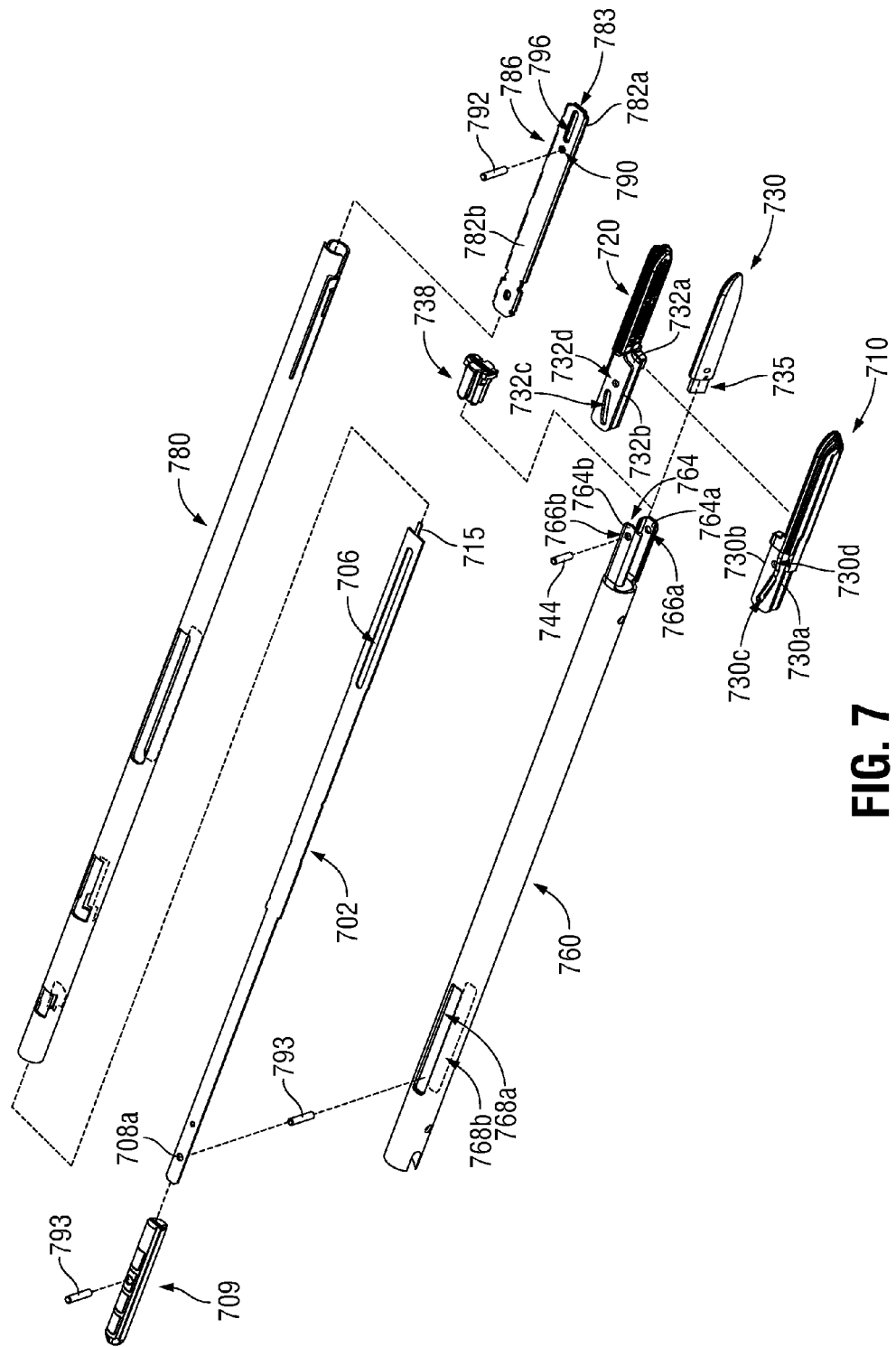
FIG. 7 is an enlarged, perspective view of first, second, and third jaw members of an end-effector assembly, an outer shaft member, and components associated therewith, shown with parts separated, in accordance with an embodiment of the present disclosure.

Referring now to FIG. 7, an outer shaft member 760 defines an exterior surface of an elongated shaft (e.g., shaft 12 shown in FIG. 1, or shaft 512 shown in FIG. 5) and supports movement of other components therethrough as described below, e.g., to impart movement to first, second and third jaw members 710, 720 and 730, respectively. An inner shaft member 780 is received within the outer shaft member 760 and is configured for longitudinal motion with respect to the outer shaft member 760. A drive guide 786 includes sidewalls 782a, 782b and is received within a distal end of the inner shaft member 780, wherein the inner shaft member 780 surrounds a portion of the drive guide 786. Sidewalls 782a, 782b define a longitudinal slot 783 through the drive guide 786 that provides lateral support to an axially reciprocatable drive member 702.

Drive guide 786 includes a through bore 790 extending through the sidewalls 782a, 782b for receiving a cam pin 792. Distally of a through bore 790, a longitudinal slot 796 is defined through the sidewalls 782a, 782b. Longitudinal slot 796 provides clearance for a pivot pin 744, and thus, permits longitudinal reciprocation of the inner shaft member 780 independent of the pivot pin 744. A longitudinal slot 706 is defined within the drive member 702 to provide clearance for the pivot pin 744 and the cam pin 792. Drive guide 786 generally includes features that cooperate with corresponding features defined in the distal end of the inner shaft member 780 to couple the drive guide 786 to the inner shaft member 780.

The outer shaft member 760 includes a pair of opposing longitudinal slots 768a, 768b defined therethrough and provided to allow longitudinal translation of a dowel pin 793 therethrough. The outer shaft member 760 defines a clevis 764 at a distal end thereof for receiving the first and second jaw members 710 and 720. Opposing vertical sidewalls 764a and 764b of the clevis 764 include respective bores 766a, 766b extending therethrough to support the pivot pin 744 and maintain an orientation of the pivot pin 744 with respect to the outer shaft member 760. A guide 738 is disposed adjacent interior surfaces of the opposing vertical sidewalls 764a and 764b of the outer shaft member 760 and includes an interior longitudinal passageway through which the axially reciprocatable drive member 702 and the drive guide 786 extend.

Pivot pin 744 extends through a proximal portion of each of the first and second jaw members 710 and 720 to pivotally support the first and second jaw members 710 and 720 at the distal end of the outer shaft member 760. A proximal portion of each of the first and second jaw members 710 and 720 is configured as a "double flag." The double flag configuration refers to the two laterally spaced parallel flanges or "flags" 730a, 730b and 732a, 732b respectively, extending proximally from a distal portion of the first and second jaw members 710 and 720. A lateral cam slot 730c and a lateral pivot bore 730d extend through each of the flags 730a, 730b of the first jaw member 710. Similarly, a lateral cam slot 732c and a lateral pivot bore 732d extend through each of the flags 732a, 732b of the second jaw member 720. Pivot bores 730d, 732d receive the pivot pin 744 in a slip-fit relation that permits the first and second jaw members 710 and 720 to pivot about the pivot pin 744 to move the first and second jaw members 710 and 720 from an open position, wherein the first and second jaw members 710 and 720 are disposed in spaced relation relative to the third jaw member 730, to a clamping or closed position, wherein the first, second and third jaw members 710, 720 and 730, respectively, cooperate to grasp tissue therebetween.

A cam 735 is operably coupled to the proximal end of the third jaw member 730 for selectively imparting movement to the third jaw member 730. A drive pin 715 is defined at the distal end of the drive member 702 and configured for engagement with the cam 735. A proximal through bore 708a extends through a proximal portion of the drive member 702 and provides a mechanism for operatively coupling the drive pin 715 to a trigger (e.g., trigger assembly 70 shown in FIG. 1, or trigger assembly 570 shown in FIG. 6) via a dowel pin 793.

In some embodiments, as shown in FIG. 7, a tube plug 709 is disposed within the inner shaft member 780 and serves to limit the passage of fluid and gas through the elongated shaft. Tube plug 709 includes features that permit longitudinal translation of the drive member 702 therethrough.

Figure 8:
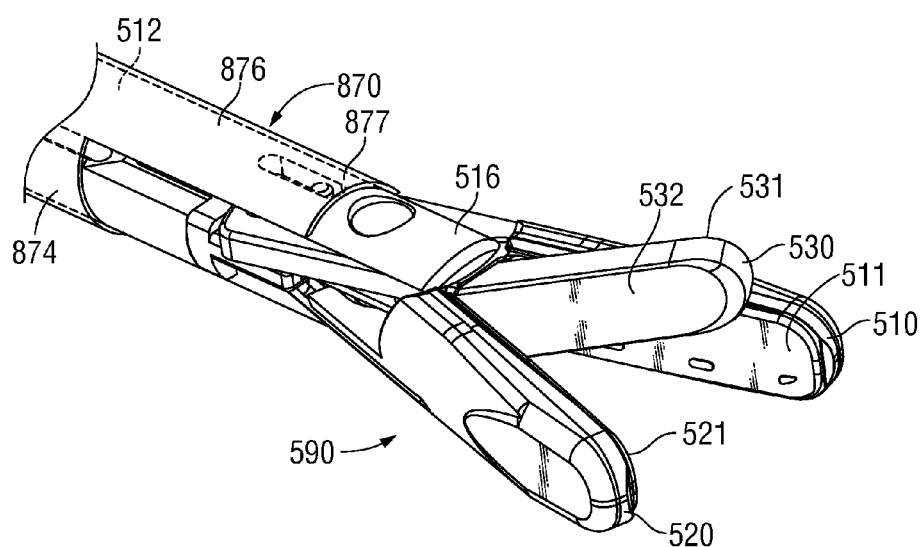
FIG. 8 is an enlarged, perspective view of the end-effector assembly shown in FIG. 5, shown with a slideably-movable drive member configured to impart movement to the third jaw member, showing the drive member disposed in a first configuration wherein the drive member is disposed in a retracted position, in accordance with an embodiment of the present disclosure.
Figure 9:
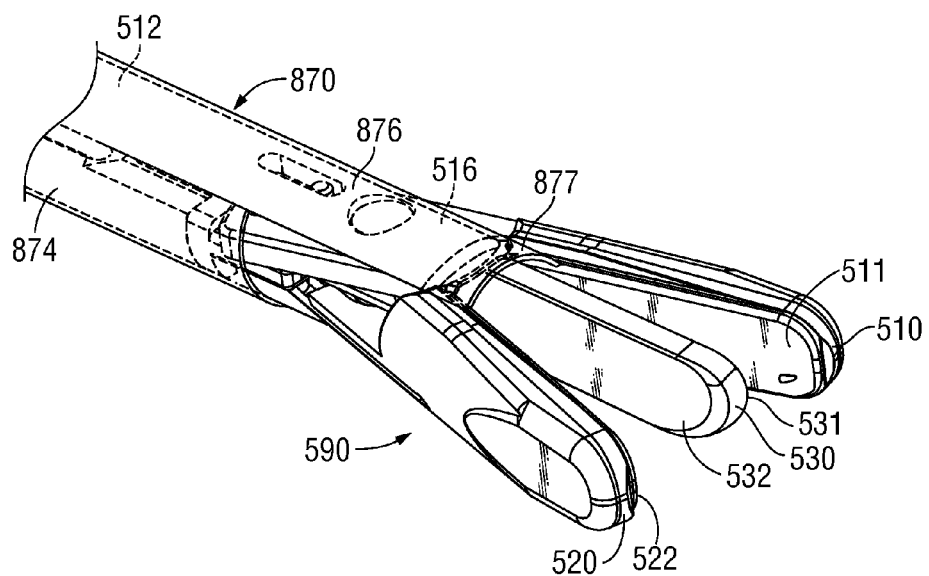
FIG. 9 is an enlarged, perspective view of the end-effector assembly shown in FIG. 5, shown with a slideably-movable drive member configured to impart movement to the third jaw member, showing the drive member disposed in a second configuration wherein the drive member is disposed in an extended position, in accordance with an embodiment of the present disclosure.

FIGS. 8 and 9 show a distal portion of the shaft 512 and the end-effector assembly 590 of the surgical instrument 500 shown in FIG. 5, shown with a drive member 870 disposed in association with the shaft 512 and configured to selectively impart movement to the third jaw member 530. In some embodiments, the surgical instrument 500 may additionally, or alternatively, include a pulley operatively coupled to the third jaw member 530 to assist in imparting movement to the third jaw member 530. Although the drive member 870 shown in FIGS. 8 and 9 is configured to impart movement to the third jaw member 530 shown in FIG. 5, it is to be understood that the drive member 870 is compatible with any of the above embodiments of an end-effector assembly including three jaw members.

Drive member 870 includes a first portion 874 and a second portion 876 extending distally therefrom. In some embodiments, as shown in FIGS. 8 and 9, the first portion 874 has a generally tubular shape, but other shapes may be utilized. The second portion is configured to engage the proximal end of the third jaw member 530. Drive member 870 is configured to be slideably-movable about the elongated shaft 512 from a first configuration wherein the drive member 870 is disposed in a retracted position (FIG. 8), in which the distal end 877 of the second portion 876 is positioned proximally to the distal end 516 of the shaft 512, to a second configuration wherein the drive member 870 is disposed in an extended position (FIG. 9), in which the distal end 877 of the second portion 876 is positioned proximally to the distal end 516 of the shaft 512.

When the drive member 870 is disposed in the extended position, as shown in FIG. 9, the distal end of the second portion 876 engages the proximal end of the third jaw member 530 and the resultant force applied to the third jaw member 530 moves the third jaw member 530. In some embodiments, the end-effector assembly 590 is configured to allow the third jaw member to be movable from a first configuration, wherein an upper surface of the third jaw member is substantially coplanar with the upper surfaces of the first and second jaw members, to a second configuration, wherein the upper surface of the third jaw member is disposed below (or above) a plane defined by the upper surfaces of the first and second jaw members.

Figure 10:
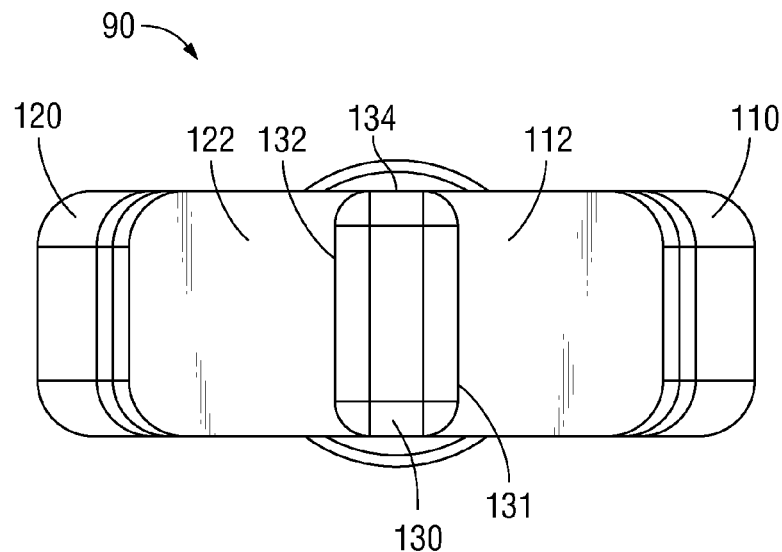
FIG. 10 is an enlarged, end view of the surgical instrument shown in FIG. 1, showing the end-effector assembly in a first configuration wherein the first and second jaw members are spaced apart from the third jaw member disposed therebetween, in accordance with an embodiment of the present disclosure.

FIG. 10 shows a portion of the surgical instrument of FIG. 1 with the end-effector assembly 90 in a first configuration wherein the first and second jaw members 110 and 120 are disposed in spaced relation relative to the third jaw member 130 disposed therebetween.

Figure 11:
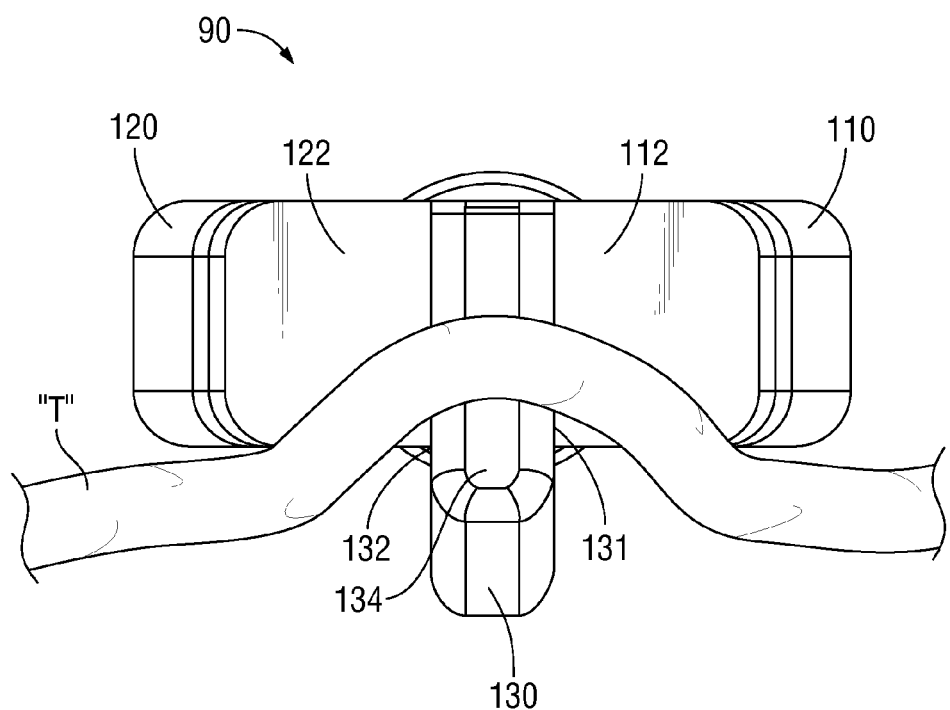
FIG. 11 is an enlarged, end view of the surgical instrument shown in FIG. 1, showing the end-effector assembly disposed in a second configuration wherein the first and second jaw members are spaced apart from the third jaw member which is aligned at a first angle, shown with tissue disposed below the lower surfaces of the first and second jaw members and tissue overlying the upper surface of the third jaw member, in accordance with an embodiment of the present disclosure.

FIG. 11 shows the end-effector assembly 90 disposed in a second configuration wherein the first and second jaw members 110 and 120 are disposed in spaced relation relative to the third jaw member 130, as shown in FIG. 10, and the third jaw member 130 is aligned at a first angle, e.g., relative to a longitudinal axis "A-A" defined by the shaft 12 (FIG. 1), such that the distal end of the third jaw member 130 is positioned below a plane defined by the distal end of the first and second jaw members 110 and 120. In FIG. 11, tissue "T", e.g., vascular tissue, is shown disposed below the lower surfaces of the first and second jaw members 110 and 120 and overlying the upper surface 134 of the third jaw member 130.

Figure 12:
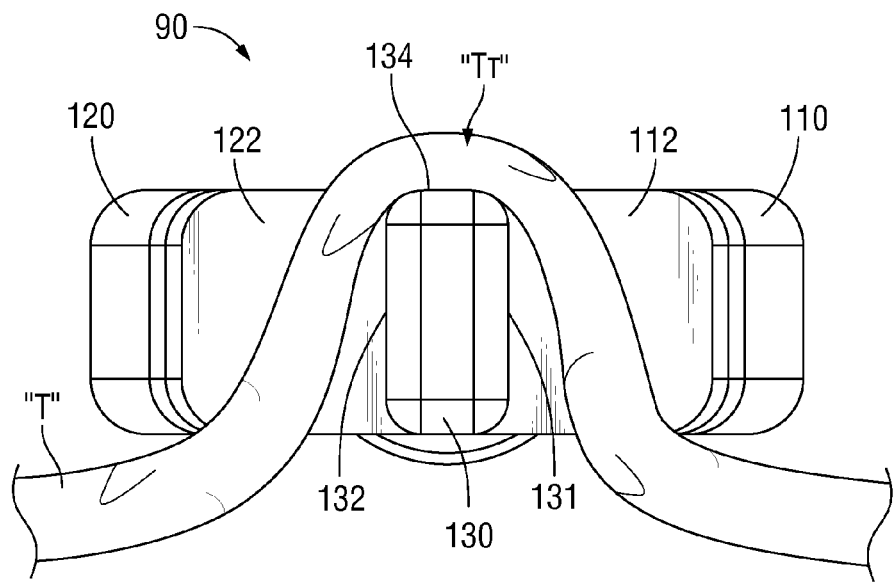
FIG. 12 is an enlarged, end view of the surgical instrument shown in FIG. 11, showing the end-effector assembly with tissue disposed between the electrically-conductive tissue-engaging surfaces of the third jaw member and the electrically-conductive tissue-engaging surfaces of the first and second jaw members, respectively, and tissue in tension overlying the upper surface of the third jaw member in accordance with an embodiment of the present disclosure.

In FIG. 12, the first and second jaw members 110 and 120 are shown disposed in spaced relation relative to the third jaw member 130, with tissue "T" disposed between the electrically-conductive tissue-engaging surfaces of the third jaw member and the electrically-conductive tissue-engaging surfaces of the first and second jaw members 110 and 120, respectively, and with tissue in tension "$T_T$" overlying the upper surface 134 of the third jaw member 130.

FIG. 13 shows the first and second jaw members 110 and 120 in a closed configuration with tissue in compression "$T_c$" disposed between the electrically-conductive tissue-engaging surfaces of the third jaw member and the electrically-conductive tissue-engaging surfaces of the first and second jaw members, respectively, shown with tissue in tension "$T_T$" overlying the upper surface 134 of the third jaw member 130. The application of energy to the tissue in compression "$T_c$" may effect cauterization, coagulation, desiccation, and/or sealing of blood vessels in the tissue in compression "$T_c$". The tissue in tension "$T_T$" may weaken, shrink, and/or divide during the application of energy to the tissue in compression "$T_c$".

The above-described surgical instruments with an end-effector assembly including three jaw members are configured to allow the surgeon to move first and second jaw members from an open position, wherein the first and second jaw members are disposed in spaced relation relative to a third jaw member disposed therebetween, to a clamping or closed position, wherein the first, second and third jaw members, cooperate to grasp tissue therebetween. The above-described end-effector assemblies are configured to allow the first and second jaw members to be controllably movable relative to one another and/or relative to the third jaw member, e.g., to control the amount of compression applied to tissue. The above-described surgical instruments are configured to provide a user capability to controllably move the first and second jaw members laterally towards the third jaw member to progressively tension the tissue overlying the upper surface of the third jaw member.

The above-described surgical instruments with an end-effector assembly including three jaw members are configured to allow the third jaw member to be movable from a first configuration, wherein an upper surface of the third jaw member is substantially coplanar with the upper surfaces of the first and second jaw members, to a second configuration, wherein the upper surface of the third jaw member is disposed below (or above) a plane defined by the upper surfaces of the first and second jaw members.

The above-described surgical instruments with an end-effector assembly including three jaw members may be suitable for sealing, cauterizing, coagulating/desiccating and/or cutting vessels and vascular tissue. The above-described surgical instruments with an end-effector assembly including three jaw members may be suitable for utilization in endoscopic surgical procedures and/or suitable for utilization in open surgical applications. The above-described surgical instruments with an end-effector assembly including three jaw members may be configured for use with a variety of energy sources.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A surgical device, comprising:
   an elongated shaft having an end-effector assembly at a distal end thereof, the end-effector assembly including movable first, second and third jaw members, the first and second jaw members controllably movable from a first position, wherein the first and second jaw members are disposed in spaced relation relative to the third jaw member disposed therebetween, to a second position, wherein the first, second and third jaw members cooperate to grasp tissue therebetween, wherein the first jaw member is movable in a first direction toward the third jaw member and the second jaw member is movable in a second direction opposite the first direction toward the third jaw member to grasp tissue therebetween, and wherein the first, second, and third jaw members are movable to a position where an upper surface of the third jaw member is coplanar with upper surfaces of the first and second jaw members and the upper surface of the third jaw member is disposed above a plane defined by bottom surfaces of the first and second jaw members; and
   an inner shaft member disposed within the elongated shaft, the inner shaft member configured for longitudinal motion with respect to the elongated shaft to controllably move the first and second jaw members laterally towards the third jaw member to progressively tension tissue overlying the upper surface of the third jaw member.

2. The surgical device of claim 1, further comprising a housing, wherein a proximal end of the elongated shaft is received within the housing.

3. The surgical device of claim 2, further comprising a trigger assembly disposed in association with the housing and operatively coupled to the third jaw member.

4. The surgical device of claim 2, wherein the elongated shaft includes an outer shaft member and an inner shaft member slidingly disposed within the outer shaft member.

5. The surgical device of claim 4, further comprising a drive guide including sidewalls and received within a distal end of the inner shaft member, wherein the inner shaft member surrounds at least a portion of the drive guide.

6. The surgical device of claim 5, further comprising a drive member operatively coupled to the elongated shaft and configured to selectively impart movement to the third jaw member, wherein the sidewalls of the drive guide define a longitudinal slot through the drive guide that provides lateral support to the drive member.

7. The surgical device of claim 6, further comprising a cam operably coupled to a proximal end of the third jaw member for selectively imparting movement to the third jaw member.

8. The surgical device of claim 7, wherein the drive member includes a first portion and a second portion extending distally from the first portion, the second portion configured to engage a proximal end of the third jaw member.

9. The surgical device of claim 7, wherein the drive member includes a drive pin defined at the distal end of the drive member and configured for engagement with the cam.

10. An end-effector assembly operatively coupled to a shaft, the end-effector assembly comprising:
    first and second jaw members pivotably mounted with respect to one another; and
    a third jaw member disposed between the first and second jaw members,
    wherein the first and second jaw members are configured to move from a first position, wherein the first and second jaw members are disposed in spaced relation relative to the third jaw member, to a second position, wherein the first, second and third jaw members cooperate to grasp tissue therebetween, wherein the first jaw member is movable in a first direction toward the third jaw member and the second jaw member is movable in a second direction opposite the first direction toward the third jaw member to grasp tissue therebetween, and wherein the first, second, and third jaw members are movable to a position where an upper surface of the third jaw member is coplanar with upper surfaces of the first and second jaw members and the upper surface of the third jaw member is disposed above a plane defined by bottom surfaces of the first and second jaw members, wherein the first and second jaw members are configured to be controllably movable towards the third jaw member to progressively tension tissue overlying the upper surface of the third jaw member.

11. The end-effector assembly of claim 10, wherein the third jaw member is configured to be controllably movable relative to a longitudinal axis defined by the shaft.

12. The end-effector assembly of claim 10, wherein the first jaw member is coupled to a first electrically-conductive tissue-engaging surface.

13. The end-effector assembly of claim 12, wherein the second jaw member is coupled to a second electrically-conductive tissue-engaging surface.

14. The end-effector assembly of claim 13, wherein the first and second electrically-conductive tissue-engaging surfaces are configured to be connectable to a source of energy.

* * * * *